US008443279B1

(12) United States Patent
Hameed et al.

(10) Patent No.: US 8,443,279 B1
(45) Date of Patent: May 14, 2013

(54) VOICE-RESPONSIVE ANNOTATION OF VIDEO GENERATED BY AN ENDOSCOPIC CAMERA

(75) Inventors: Salmaan Hameed, San Jose, CA (US); Amit A. Mahadik, San Jose, CA (US); Kiran A. Javadekar, San Jose, CA (US); Prabhu Raghavan, San Jose, CA (US); Nirali M. Verma, San Jose, CA (US); Anantharaman Balasubramanian, San Jose, CA (US)

(73) Assignee: Stryker Corporation, Kalamazoo, MI (US)

( * ) Notice: Subject to any disclaimer, the term of this patent is extended or adjusted under 35 U.S.C. 154(b) by 1685 days.

(21) Appl. No.: 10/965,568

(22) Filed: Oct. 13, 2004

(51) Int. Cl.
*G06F 17/00* (2006.01)

(52) U.S. Cl.
USPC ............................ 715/230; 715/233; 715/201

(58) Field of Classification Search .......... 715/230–233, 715/201–203
See application file for complete search history.

(56) References Cited

U.S. PATENT DOCUMENTS

| | | | |
|---|---|---|---|
| 4,184,048 A | 1/1980 | Alcaide | |
| 4,482,998 A | 11/1984 | Marouf et al. | |
| 4,499,578 A | 2/1985 | Marouf et al. | |
| 4,672,669 A | 6/1987 | DesBlache et al. | |
| 5,767,897 A * | 6/1998 | Howell | 348/14.07 |
| 5,877,819 A * | 3/1999 | Branson | 348/701 |
| 5,878,394 A | 3/1999 | Muhling | |
| 5,880,788 A * | 3/1999 | Bregler | 348/515 |
| 6,031,526 A * | 2/2000 | Shipp | 715/201 |
| 6,192,339 B1 | 2/2001 | Cox | |
| 6,397,181 B1 * | 5/2002 | Li et al. | 704/256.4 |
| 6,453,020 B1 | 9/2002 | Hughes et al. | |
| 6,463,361 B1 | 10/2002 | Wang et al. | |
| 6,496,107 B1 | 12/2002 | Himmelstein | |
| 6,647,535 B1 * | 11/2003 | Bozdagi et al. | 715/255 |
| 6,675,352 B1 * | 1/2004 | Osaki et al. | 715/203 |
| 6,687,877 B1 * | 2/2004 | Sastry et al. | 715/201 |
| 6,791,601 B1 | 9/2004 | Chang et al. | |
| 6,842,190 B1 * | 1/2005 | Lord et al. | 348/231.5 |
| 6,842,510 B2 | 1/2005 | Sakamoto | |
| 7,127,392 B1 | 10/2006 | Smith | |
| 7,236,929 B2 | 6/2007 | Hodges | |
| 7,292,689 B2 * | 11/2007 | Odinak et al. | 379/265.09 |
| 2002/0072912 A1 | 6/2002 | Yen et al. | |
| 2002/0129057 A1 * | 9/2002 | Spielberg | 707/512 |
| 2002/0145622 A1 * | 10/2002 | Kauffman et al. | 345/723 |
| 2002/0194197 A1 * | 12/2002 | Flank | 707/104.1 |
| 2003/0033347 A1 * | 2/2003 | Bolle et al. | 709/107 |
| 2003/0182052 A1 * | 9/2003 | DeLorme et al. | 701/201 |
| 2004/0172247 A1 * | 9/2004 | Yoon et al. | 704/251 |
| 2004/0260558 A1 * | 12/2004 | Loui et al. | 704/272 |
| 2004/0260577 A1 * | 12/2004 | Dahlin et al. | 705/2 |

OTHER PUBLICATIONS

"Stryker Endoscopy, Desktop Pro, User's Guide", pp. 1-29, Stryker Endoscopy, San Jose, CA, 2002.
G.F. Buess et al., "A New Remote-Controlled Endoscope Positioning System for Endoscopic Solo Surgery", The FIPS Endoarm, Surgical Endoscopy Ultrasound and Intervention Techniques, Springer-Verlag New York Inc., Jul. 9, 1999, pp. 395-399.

\* cited by examiner

*Primary Examiner* — Thu Huynh
(74) *Attorney, Agent, or Firm* — Blakely, Sokoloff, Taylor & Zafman LLP

(57) ABSTRACT

An image capture device in an endoscopic imaging system receives a video stream generated by an endoscopic video camera. In response to automatic recognition of a spoken utterance while the video stream is being received from the endoscopic video camera, the image capture device associates with the video stream an annotation that corresponds to the spoken utterance. The image capture device provides the video stream to a display device for display, such that the annotation can be overlaid on one or more frames of the video stream displayed on the display device.

28 Claims, 11 Drawing Sheets

VOICE-RESPONSIVE ANNOTATION OF VIDEO GENERATED BY AN ENDOSCOPIC CAMERA

FIELD OF THE INVENTION

At least one embodiment of the present invention pertains to endoscopic imaging systems, and more particularly, to a method and apparatus annotate video generated by an endoscopic camera in response to speech.

BACKGROUND

Endoscopy in the medical fields allows internal features of a patient's body to be viewed without the use of traditional, fully-invasive surgery. Endoscopy is widely used to perform minimally-invasive medical procedures, such as arthroscopy, laparoscopy, gastroscopy, colonoscopy, etc.

A medical endoscopic imaging system includes an endoscope (or simply "scope"), one end of which is inserted into the body of a patient while the other end of the scope is coupled to a video camera. The scope may be a rigid scope, such as used in arthroscopy or laparoscopy, or a flexible scope, such as used in gastroscopy or colonoscopy. Images acquired by the camera are typically provided to, and displayed on, a conventional display device, such as a cathode ray tube (CRT) or liquid crystal display (LCD) based monitor, which displays live video. A high intensity light source is normally coupled to the scope by a fiber optic cable, to transmit light through the scope to into the patient's body. The camera may also be coupled to various peripheral devices, such as a printer, an image capture unit, and a video recorder. At least a portion of the endoscopic procedure is normally recorded on video.

Typically, after completion of a medical procedure, the physician dictates notes about the procedure, describing exactly what was done during the procedure, observations the physician made during the procedure, medications administered, etc. The physician typically dictates these notes into some form of audio recording device or system. If the medical procedure was recorded on video, the physician might dictate his notes while viewing the recorded video, perhaps mentioning in his dictation the timestamps of certain key frames and what was happening in those frames. The dictation (audio recording) may be provided to a transcription service, which produces a written record of the dictation for the patient's file.

The physician may also generate a set of instructions for editing the recorded video; this set of instructions is sometimes called a "cut list". The video recording normally includes a displayable timestamp for each frame. The physician would typically take note of particular frames he wished to include in a presentation or edited version of the video, and then write down (or dictate) editing instructions including the timestamps of selected frames and particular actions related to those frames. For example, the physician might include in the cut list an instruction such as, "Add the two minute segment starting with frame timestamped 12:04:17 to the end of my presentation." The physician would then provide the cut list to a video technician, who would edit the video based on the cut list using special software tools. Alternatively, the physician might mention the editing instructions in his dictation, such that the transcription service could generate the cut list.

When a medical procedure such as endoscopy is recorded on video, it is desirable for a physician to be able to associate certain annotations directly with particular frames or segments of the video, to make it easier for someone viewing the video to understand what is being shown. For example, if certain frames of a video from a laparoscopy procedure show the patient's gall bladder, it might be desirable to be able to place the label "gall bladder" on top of those frames, so that the label is visible when those frames are displayed. This capability is particularly needed in endoscopy, where the field of view of the video camera is extremely small, often making it difficult for an observer to determine the context and to discern what is being shown. However, such capability is not known to be provided in the prior art.

SUMMARY OF THE INVENTION

One aspect of the present invention is a method that includes receiving a video stream generated by an endoscopic video camera and, in response to automatic recognition of a spoken utterance while the video stream is being received from the endoscopic video camera, associating an annotation that corresponds to the spoken utterance with at least a portion of the video stream. Other aspects of the invention include an apparatus and a system which can perform such a method.

In yet another aspect of the invention, in response to a predetermined input, a set of one or more frames in a recorded video stream from an endoscopic video camera, each of which has an annotation previously associated therewith, is identified. An album display is then generated in which each frame in the set is displayed as a thumbnail image in proximity with the associated annotation.

In still another aspect of the invention, a search term specified by a user is input, and a set of stored annotations associated with at least a portion of the recorded video stream is searched for the search term. If an annotation corresponding to the search term is found in the set of stored annotations, a visual representation of a segment of the recorded video stream associated with the annotation is caused to be displayed to the user.

Other aspects of the invention will be apparent from the accompanying figures and from the detailed description which follows.

BRIEF DESCRIPTION OF THE DRAWINGS

One or more embodiments of the present invention are illustrated by way of example and not limitation in the figures of the accompanying drawings, in which like references indicate similar elements and in which.

DETAILED DESCRIPTION

A method and apparatus to automatically annotate video generated by an endoscopic camera in response to speech are described. In particular, and as described further below, an endoscopic imaging system according to certain embodiments of the invention includes: an endoscopic video camera; a voice-responsive control system (VCS) that includes an automatic speech recognition (ASR) engine; and an image capture device. The VCS receives speech from a user to control functions of various components in the endoscopic imaging system, including the image capture device. The image capture device receives a video stream generated by an endoscopic video camera and captures video and/or still images from the video stream. In response to automatic recognition of a spoken utterance by the ASR engine, while the video stream is being received from the endoscopic video camera, the image capture device identifies an annotation that corresponds to the utterance and associates the annotation with the video stream. The annotation can be, for example, text, a non-text visual (e.g., graphical) object, or an audio object. The image capture device provides the video stream to a display device for display, where the annotation is overlaid on one or more corresponding frames of the displayed video.

Figure 1:
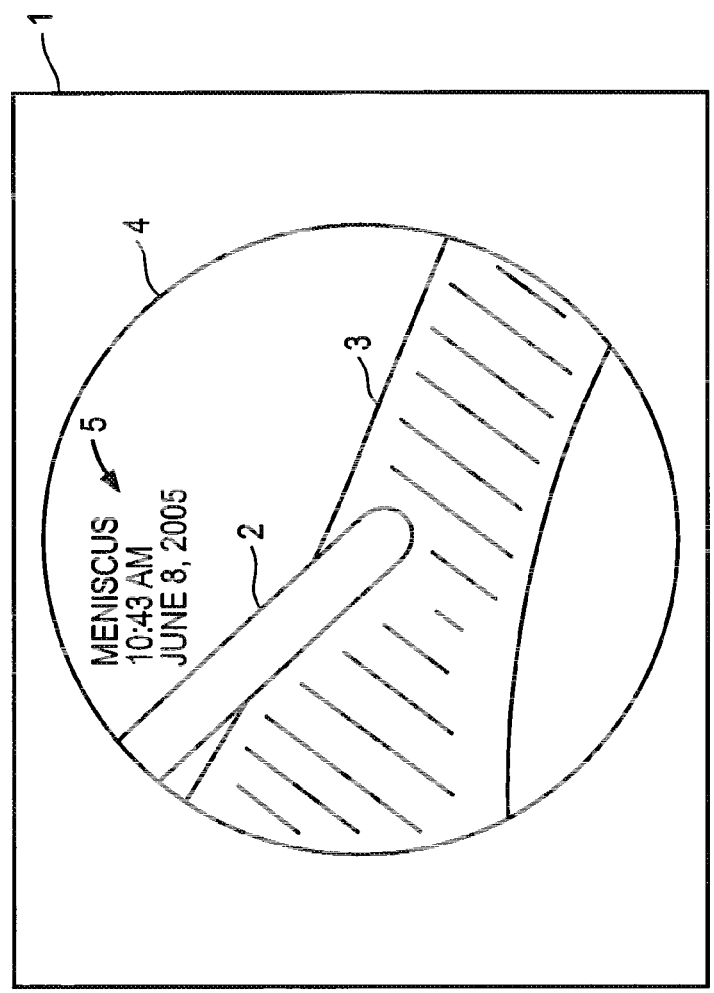
FIG. 1 illustrates an example of a display of video generated by an endoscopic video camera.

So for example, refer to FIG. 1, which illustrates a display 1 of video generated by an endoscopic video camera during an arthroscopy. A surgical tool 2 and the patient's meniscus 3 are visible in the field of view 4. However, what is being shown may not be readily apparent to someone else viewing a recording of the video at a later time. Therefore, during the procedure the physician can speak a predetermined command and then the word "meniscus" into a microphone connected to the VCS. This action will cause the word "meniscus" to be recognized and associated with a predetermined number of currently displayed frames of the live video, as an annotation. This will also cause the text annotation "MENISCUS" 5 to be overlaid on (displayed on top of) those frames in the live display and in the recording of the video, such as shown in FIG. 1. Annotating the video in this manner makes it easier for someone later viewing a recording of the video to understand what is being shown.

Because annotations are associated with the appropriate video frames automatically in response to the user's speech, the technique described herein is much faster and easier than the prior art techniques of annotating video. Furthermore, annotating video frames in this way facilitates subsequent location and viewing of particular frames of interest by using a conventional, software-based keyword search tool. For example, by using such a search tool, a user can search the recorded video for the annotation "gall bladder" in order to locate frames that show the gall bladder. Associating annotations with certain frames allows the physician or other user (hereinafter "user") to identify frames considered to be of particular interest without having to view the entire recorded video. The annotation feature can also be used to generate an "album" display of thumbnail versions of the key frames along with their annotations. From such a display, corresponding segments of video can be played back, and annotations can be added, deleted or modified by the user.

Note that annotations do not have to be text. An annotation can be, for example, a non-text visual object, such as a pointer or a hollow shape used to point to or outline (respectively) an anatomical feature. Similarly, an annotation can be an audio object; for example, an audio recording of the spoken phrase "gall bladder" can be associated with particular frames of video, such that that phrase will be played back through an audio speaker when those video frames are played back. This feature is particularly useful if the video is a pure video stream, not an audiovisual stream (i.e., when there is no audio associated with the video, other than audio annotations created by the user). A physician may want to record all of the audio during a particular segment of video, so that he can more easily explain what is being done during a segment. This feature can be activated by speaking a predetermined command.

Figure 2B:
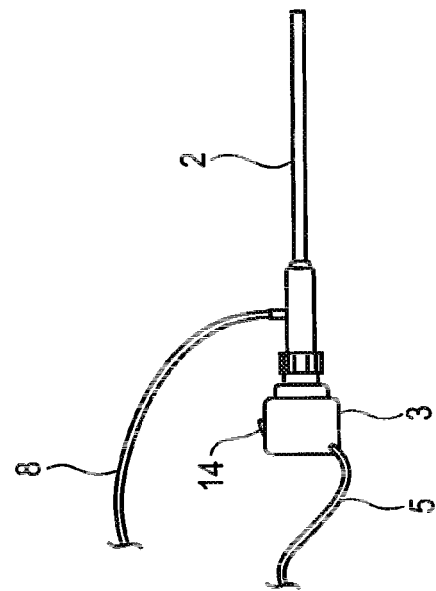
FIGS. 2A and 2B collectively show an example of an endoscopic imaging system.
Figure 2A:
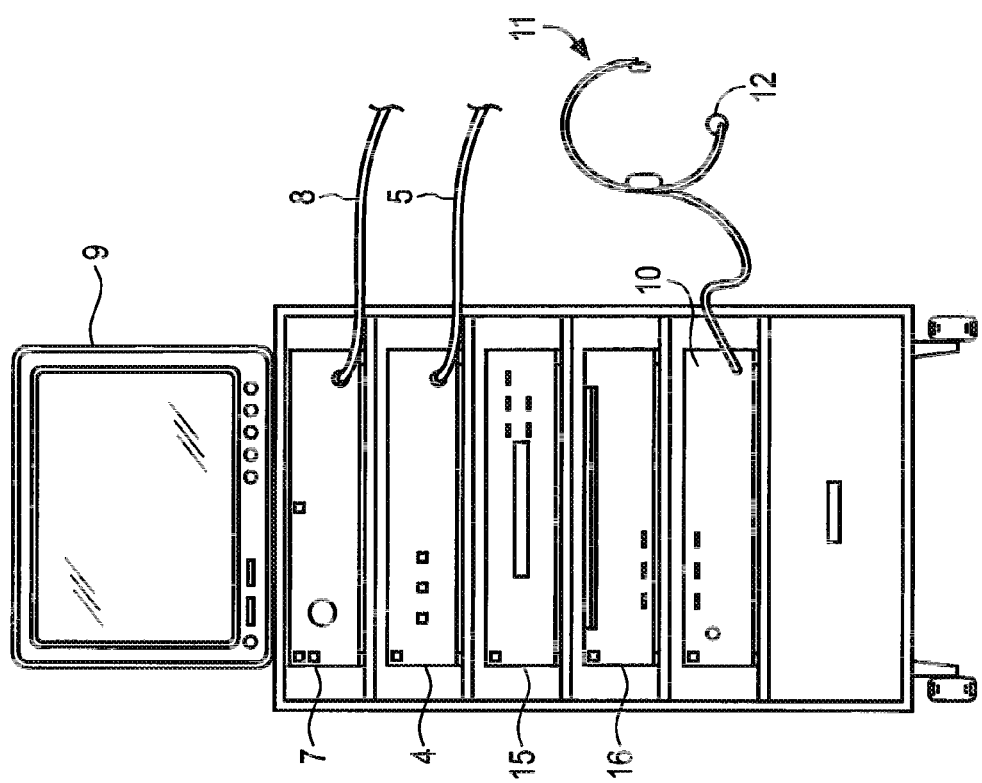

Refer now to FIGS. 2A and 2B, which collectively show an example of an endoscopic imaging system in which the annotation technique introduced herein can be implemented. The illustrated system includes an endoscope ("scope") 2 of the type commonly used for laparoscopy or arthroscopy. The scope 2 is coupled to an endoscopic video camera 3, which includes well-known components for generating color video, based on light received through the scope 2. High intensity light is transmitted into the body of the patient from a light source unit 7 through fiber optic cable 8 and the scope 2. The camera 3 is coupled to camera control unit (CCU) 4 by a flexible electronic transmission line 5. Certain functions of the camera 3 can be controlled from CCU 4. Transmission line 5 conveys video data from the camera 3 to the CCU 4 and also conveys various control signals bi-directionally between the camera 3 and the CCU 4. One or more buttons 14 or other similar manual controls on the camera 3 allows a user to control certain functions of the camera system, such as zoom.

Certain functions of the system may also be controlled by voice commands using a voice-responsive control system (VCS) 10. Speech from a user is input to the VCS 10 through a microphone 12 on a headset 11 worn by the user. The VCS 10 includes an ASR (not shown in FIG. 2) to recognize and generate control signals in response to the user's speech.

Also coupled to the CCU 4 are an image capture device (ICD) 15, a printer 16, and perhaps other devices (not shown), as desired. Video acquired by camera 3 is optionally processed by CCU 4 and used to generate images which are displayed on monitor 9. The ICD 15 can record the live video and/or generate static images (i.e. captured video frames) from the live video. Hard copies of capture video frames can be printed by the printer 16.

Figure 3:
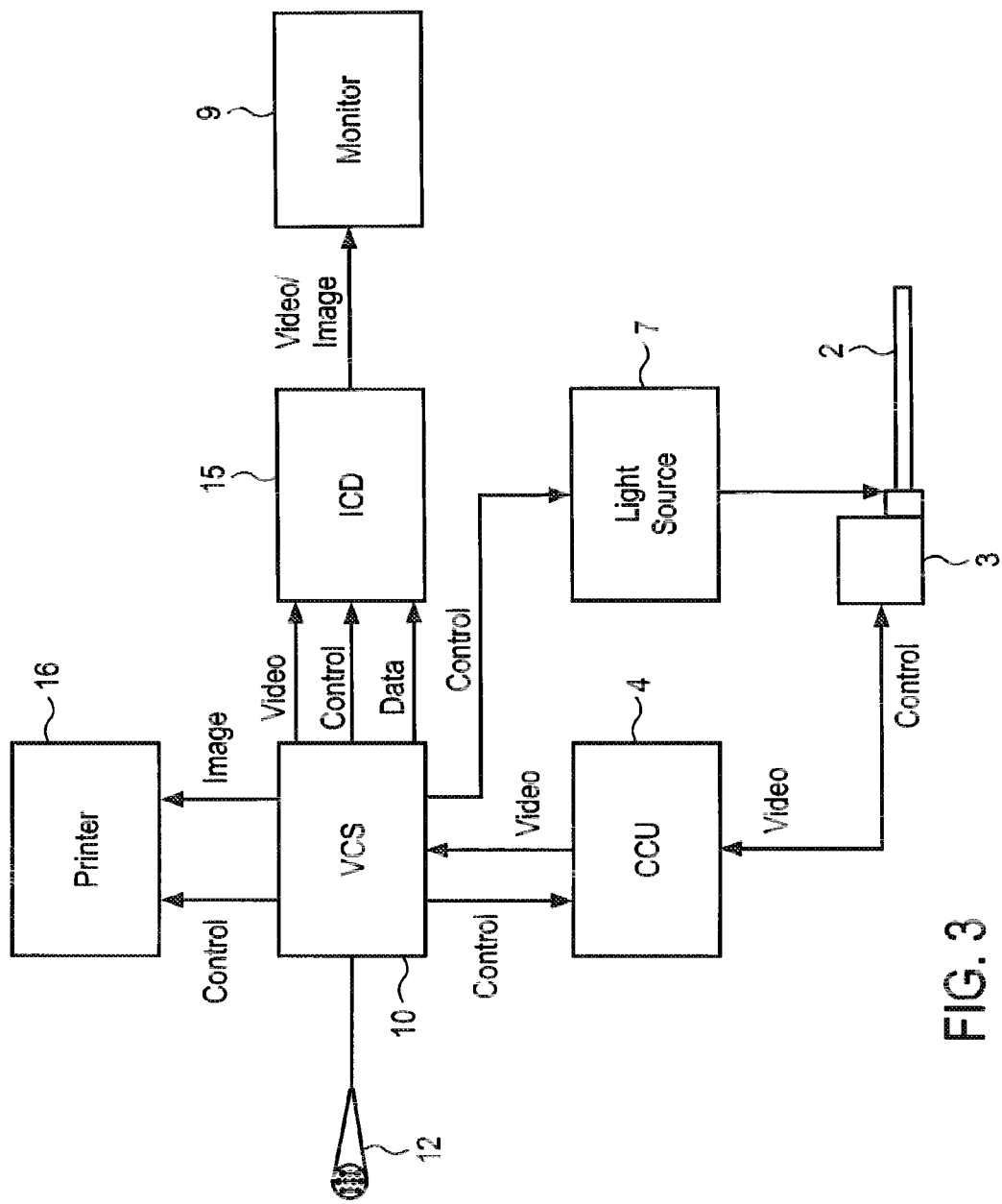
FIG. 3 is a functional block diagram of the endoscopic camera system of FIG. 1.

FIG. 3 is a functional block diagram of the endoscopic camera system of FIG. 1, according to certain embodiments of the invention. The CCU 4 provides certain basic video processing functions and enables control certain camera functions, such as control of white balance control, contrast, zoom, etc. Details of the architecture, capabilities and operation of the CCU 4 are not germane to the present invention and therefore need not be described herein.

The VCS 10 provides centralized voice-based control of various devices in the operating room, including any or all of: the CCU 4, the ICD 15, the light source unit 7, the monitor 9, and the printer 16. For each device to be controlled in the operating room, the VCS 10 provides a hierarchy of commands that can be spoken by a user to control that device. By simply speaking the name of a device into the microphone 12, the user can access the menu of commands for that device. An example of a device suitable for use as the VCS 10 is the Stryker Integrated Device Network (SIDNE) system from Stryker Endoscopy of San Jose, Calif. The VCS 10 provides separate control outputs CTRL to each of the voice-controllable devices. In addition, the VCS 10 provides separate video and data outputs to at least the ICD 15.

The ICD 15 is multi-function digital image capture device. The ICD 15 receives video generated by the endoscopic camera 3 (either directly or through one or more other devices)

and provides video output to the external monitor 9 and/or its own built-in display device. The ICD 15 provides the ability to capture live video, i.e., to convert standard analog video into digital format (if necessary) and to record the digital video, and to capture video frames as still images. In certain embodiments, the ICD 15 also provides various other capabilities, including the ability to stream live or recorded video over a computer network. An example of a device suitable for use as the ICD 15 is one of the Stryker Digital Capture (SDC) devices from Stryker Endoscopy, such as the Stryker SDC Pro, SDC Pro 2, or SDC HD.

In certain embodiments of the invention, the ability to annotate live video based on speech is provided by cooperation of the VCS 10 with the ICD 15. Live video generated by the camera 3 is routed through the CCU 4 to the VCS 10 and then to the ICD 15. Routing the video through the VCS 10 facilitates synchronization of spoken annotations with the live video stream. In other embodiments, the functions of the VCS 10 and the ICD 15 may be provided in a single integrated unit. In addition, the video could alternatively be routed directly from the CCU 4 to the ICD 15 if some other way of synchronizing the audio and the video is provided.

Figure 4:
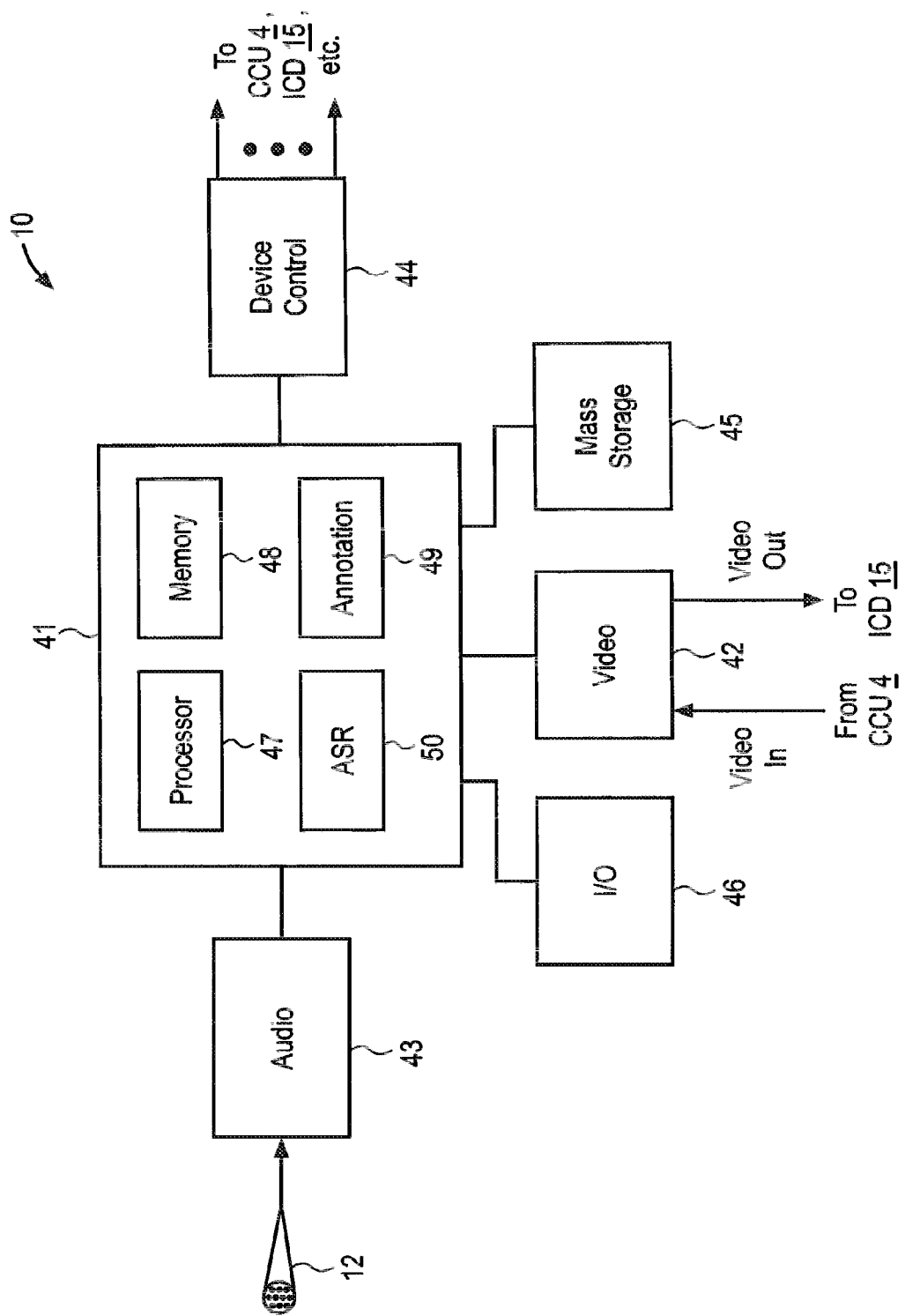
FIG. 4 is a block diagram of the voice-responsive control system (VCS)

FIG. 4 is a block diagram showing the VCS 10 in greater detail. As illustrated, the VCS 10 includes a motherboard 41 coupled to a video board 42, an audio board 43, a device control interface 44, a mass storage device 45, and various I/O controls and/or indicators 46. The motherboard 41 includes one or more processors 47 or other similar control devices as well as one or more memory devices 48. The processor 47 controls the overall operation of the VCS 10 and can include hardwired circuitry, programmable circuitry that executes software, or a combination thereof. The processor 47 may, for example, execute software stored in the memory 48. The processor 47 may include, for example, one or more general- or special-purpose programmable microprocessors and/or microcontrollers, application specific integrated circuits (ASICs), programmable logic devices (PLDs), programmable gate arrays (PGAs), or the like. Memory 48 may include any combination of one or more random access memories (RAMs), read-only memories (ROMs) (which may be programmable), flash memory, and/or other similar storage devices.

In the illustrated embodiment, the motherboard 41 also includes an annotation module 49 to provide the VCS's functionality related to annotating video, as described herein. The annotation module 49 can be hardwired circuitry, programmable circuitry that executes software, or a combination thereof. Although shown as a separate unit, the annotation module 49 can be implemented in the processor 47. The annotation module 49 can alternatively be located off the motherboard 41, such as in the device control interface 44 or the audio board 43, or it can be distributed between multiple boards/devices within the VCS 10.

The video board 42 can be a simple video input/output (I/O) interface, which includes an input to receive live video from the CCU 4 and an output to provide the received live video to the ICD 15. The audio board 43 has an input to receive speech of the user from the microphone 12. In addition, the audio board 43 includes appropriate audio processing circuitry such as is well-known in the art. As noted above, the VCS 10 includes an ASR engine 50, which may be implemented on the motherboard (as shown), or on the audio board, or both. Although shown as a separate unit, the ASR engine 50 could be implemented in the form of the processor 47 executing appropriate software.

The device control board 44 provides a communication interface between the VCS 10 and other voice-controllable devices to allow the VCS 10 to control those devices. The device control board 44 may include various different types of control/communication interfaces, such as a serial interface (e.g., RS-232, FireWire, or USB), Bluetooth, infrared (IR), etc. The mass storage device 45 may be any type of nonvolatile storage device capable of storing a relatively large volume of data and/or instructions, such as a magnetic or optical disk drive. The details of how devices are controlled by the VCS 10 and the protocols used are not germane to the present invention and need not be described herein.

Figure 5:
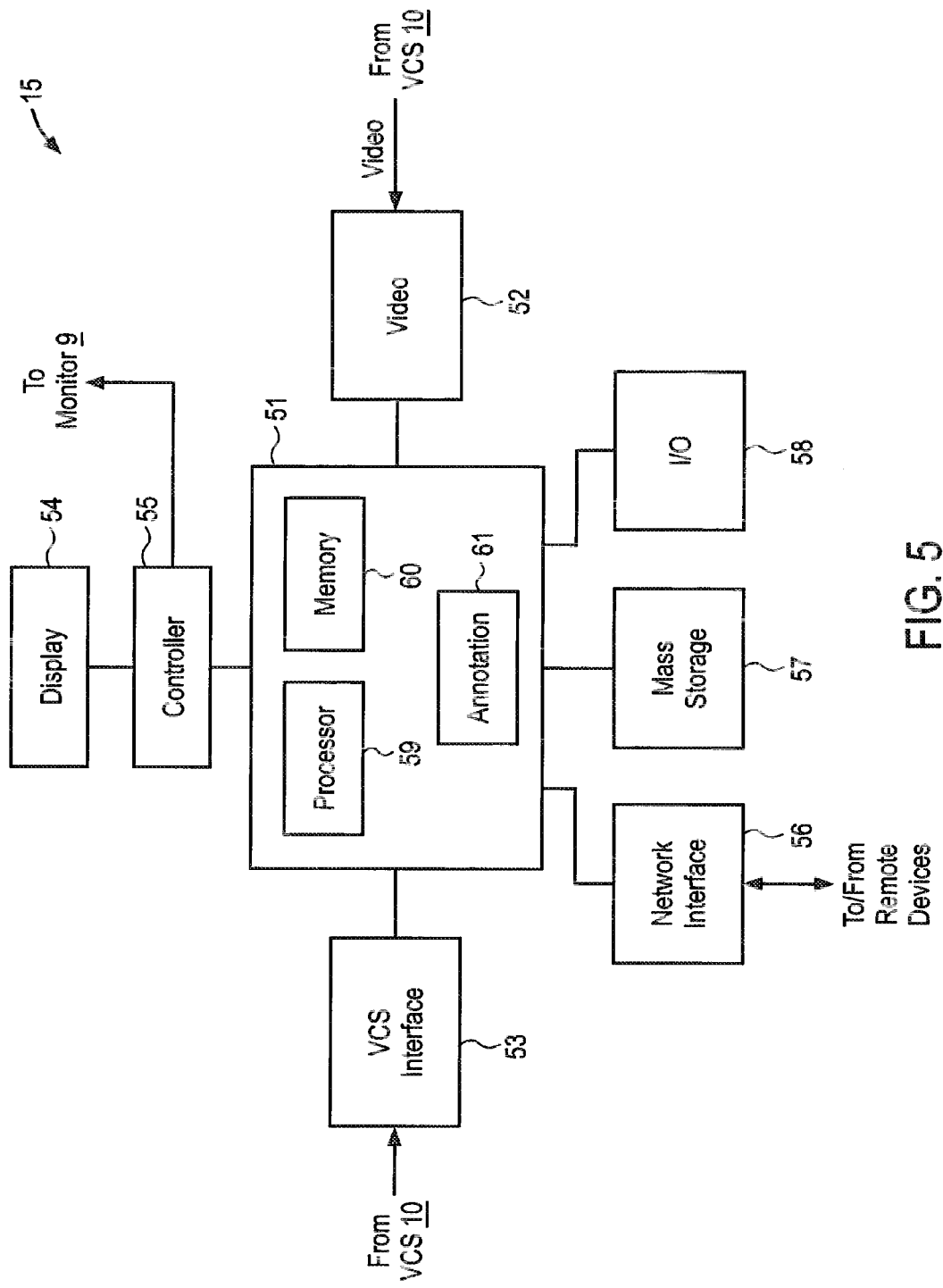
FIG. 5 is a block diagram of the image capture device (ICD)

FIG. 5 is a block diagram showing the ICD in greater detail. As illustrated, the ICD 15 includes a motherboard 51 coupled to a video board 52, a VCS interface 53, a touchscreen display 54 (via a display controller 55), a network interface 56, a mass storage device 57, and various I/O controls and/or indicators 58. The motherboard 51 includes one or more processors 59 or other similar control devices as well as one or more memory devices 60. The processor 59 controls the overall operation of the ICD 15 and can include hardwired circuitry, programmable circuitry that executes software, or a combination thereof. The processor 59 may, for example, execute software stored in memory 60. The processor 59 may be, for example, one or more general- or special-purpose programmable microprocessors and/or microcontrollers, ASICs, PLDs, PGAs, or the like. Memory 60 may include any combination of one or more random access memories (RAMs), read-only memories (ROMs) (which may be programmable), flash memory, and/or other similar storage devices.

In the illustrated embodiment, the motherboard 51 also includes an annotation module 61 to provide the ICD's functionality related to annotating video, as described herein. The annotation module 61 can be hardwired circuitry, programmable circuitry that executes software, or a combination thereof. Although shown as a separate unit, the annotation module 61 can be implemented in the form of processor 59. The annotation module 61 can alternatively be located off the motherboard 51, such as in the VCS interface 53 or the video board 52, or it can be distributed between multiple boards/devices within the ICD 15.

The built-in touch-screen display 54 is used to provide a user-friendly, touch-sensitive, graphical user interface. The VCS interface 53 is used to receive control signals and data from the VCS 10. The display controller 55 provides output to the touch-screen display 54 and/or to the external monitor 9, for display. The network interface 56 allows video, still images, electronic messages, and other information to be communicated to or from remote devices over a network.

The video board 52 receives the live video stream from the camera 3 (via the VCS 10 and/or the CCU 4) and includes video capture circuitry to convert input analog video into digital format (if it is not already in digital format) and to capture still images of individual video frames. The mass storage device 57 can be used to store recorded (annotated) video, captured still images, annotations created by the user, predefined annotations, and related metadata.

Figure 6:
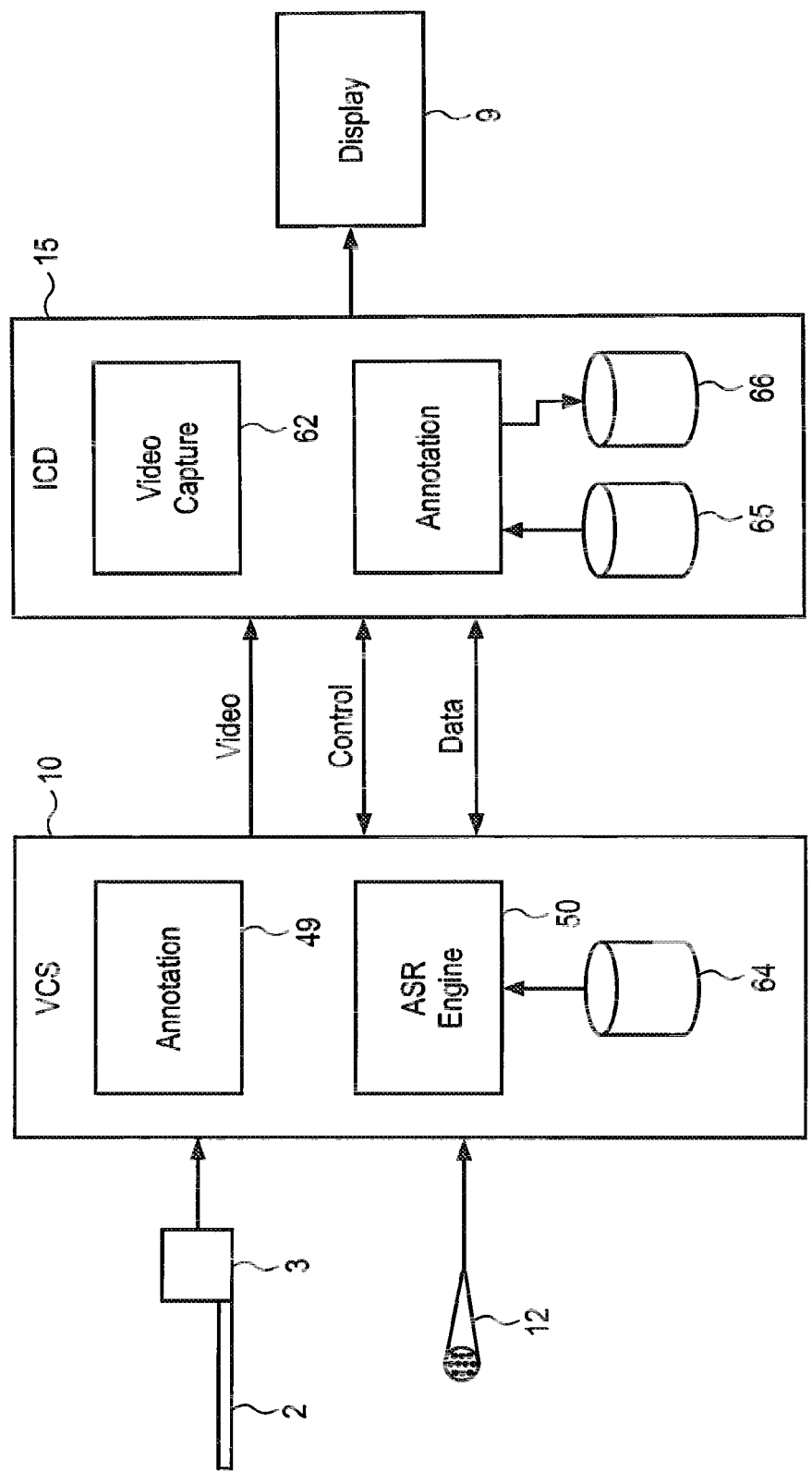
FIG. 6 illustrates in greater detail the functional relationship between the VCS and the ICD for purposes of annotating video.

FIG. 6 further illustrates the cooperation between the VCS 10 and the ICD 15 for purposes of the annotation technique introduced herein. The VCS 10 includes an annotation dictionary 64, which is a mapping of annotation phonemes to index values. The annotation dictionary 64 may be physically stored in, for example, the mass storage device 45 of the VCS 10. The phonemes in the annotation dictionary 64 are phonetic representations, in a format that can be understood by the ASR engine 50, of all annotations that can be recognized by the system. These may include annotations from default lists, annotations previously defined by the user, or a combination thereof. The index values are simply unique identifiers for each individual phoneme.

The ASR engine 50 is used to recognize spoken commands, annotations, user selections, etc. After recognizing the "Mark Video" command, for example, the ASR engine 50 will look in the annotation dictionary 64 for the phoneme of whatever speech immediately follows the command. If the ASR engine 50 finds a stored phoneme that sufficiently matches the speech which immediately followed the command, it then determines the index of that phoneme. The VCS 10 then provides that index to the ICD 15, which uses that information as described below.

The ICD 15 includes a second annotation dictionary 65, which is a mapping of the index values of all previously-defined annotations to the actual output values of those annotations. The output value of an annotation represents the form the annotation will have in the recorded video. For example, in the case of a text annotation the output value is the actual text. Similarly, the output value can be an audio wave file in the case of an audio annotation or graphics data describing a graphical object in the case of a graphical annotation.

The ICD 15 has three separate communication links with the VS 10: a Video channel, a Control channel, and a Data channel. The Video channel is the link by which the VCS 10 transmits to the ICD 15 the live video it receives from the camera 3 (via the CCU 4). The Data channel is used by the VCS 10 to enable voice-based control of various functions of the ICD 15 which are not germane to the present invention. The VCS 10 uses the Control channel to communicate with the ICD 15 for purposes of annotating video, creating and managing annotations, etc.

Figure 7:
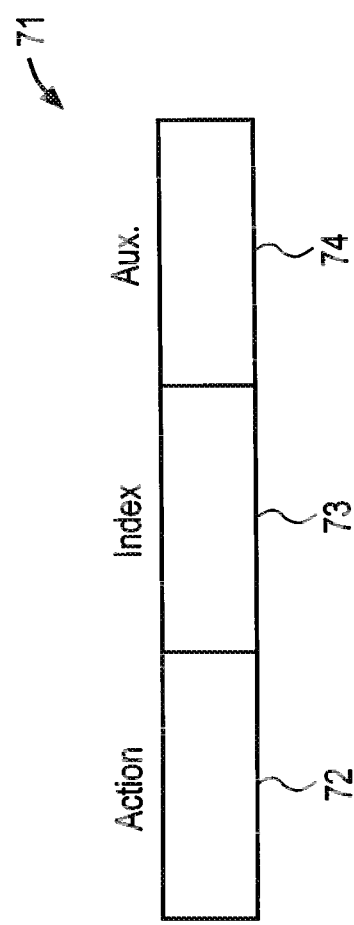
FIG. 7 shows an example of a control packet communication between the VCS and the ICD.

Control packets of a predetermined format are used to communicate on the Control channel, which is a bidirectional communication channel. For purposes of creating an annotation, the VCS 10 uses a control packet to communicate the index of the recognized annotation to the ICD. FIG. 7 shows an example of a control packet 71. In embodiments represented by FIG. 7, a control packet 1 includes three fields: an Action field 72, an Index field 73, and an Auxiliary field 74. The Action field 72 indicates which action is being requested by the user. For example, the value stored in the Action field 72 may represent any of the following actions: capture a still image from video, start recording video, stop recording video, annotate video as text, annotate video as a graphical object, and annotate video as audio. The Index field 73 contains the index of the recognized annotation, if applicable. The Auxiliary field 74 contains the (x,y) display coordinates of the annotation, if applicable (e.g., if coordinates other than the default values are to be used) and/or a flag to indicate whether text overlay is appropriate.

When the ICD 15 receives a control packet indicating that an annotation is being created (as indicated by the Action field 72), it uses the index value in the control packet to look up the output value of the annotation in its annotation dictionary 65. The output value is then associated with one or more of the live video frames that are being received from the camera 3 (via the CCU 4 and VCS 10) and captured/recorded by video capture circuitry 62. This act of associating includes storing the created output value in an appropriate annotation storage area 66 (which may be part of the video stream itself). One or both of the annotation dictionary 65 and the annotation storage area 66 may be physically stored in, for example, the mass storage device 57 of the ICD 15.

The output value of an annotation (hereinafter simply "the annotation") can be associated with one or more frames in any of several ways. In one embodiment, the annotation is associated with a frame by embedding the annotation within the closed caption region of the frame. Alternatively, the annotation can be embedded within the actual video information of the frame, by using, for example, steganography. These two approaches are advantageous because, when the recorded video is subsequently played back, the annotation can be viewed (or heard, if it is audio) using a conventional, off-the-shelf PC-based multimedia player, such as Windows Media Player. In a third embodiment, the annotation is appended to the end of the video stream. For example, one or more annotations can be stored in the form of an .ini file appended to the end-of-file (EOF) byte sequence at the end of the video stream. In that case, a special-purpose multimedia player configured to read this file is used to read the annotations. This could be done using, for example, a custom DirectShow filter that parses the indexing information at the end of a video stream before rendering the video content in the player.

As noted above, the stored set of predefined annotations may include one or more default annotation lists, annotations defined by the end user (e.g., the physician), or a combination of default annotations and user-defined annotations. To define a new annotation, the user can speak a known command, such as "Define Annotation", and then immediately thereafter speak the word or phrase which is to be the new annotation. This causes a phoneme of the new annotation to be added to the annotation dictionary 64 in the VCS 10 and a new index to be created and associated with that phoneme in annotation dictionary 64. The user may then be prompted (e.g., via a graphical user interface on the VCS 10 or the ICD 15) to provide or confirm the correct text representation of the new annotation. The annotation dictionary 65 in the ICD 15 is then updated to add the index and text of the new annotation. Alternatively, an annotation can be added by first providing its text to the ICD 15 in order to update annotation dictionary 65, and then providing the proper pronunciation of that text to the VCS 10 in order to update annotation dictionary 64. It is also possible that an annotation may be added to one of the VCS 10 or the ICD 15 while the other one is not connected or powered on. Consequently, each time the VCS 10 and ICD 15 are initially powered on and connected to each other, the Control channel is used to synchronize annotation dictionaries 64 and 65.

Figure 8:
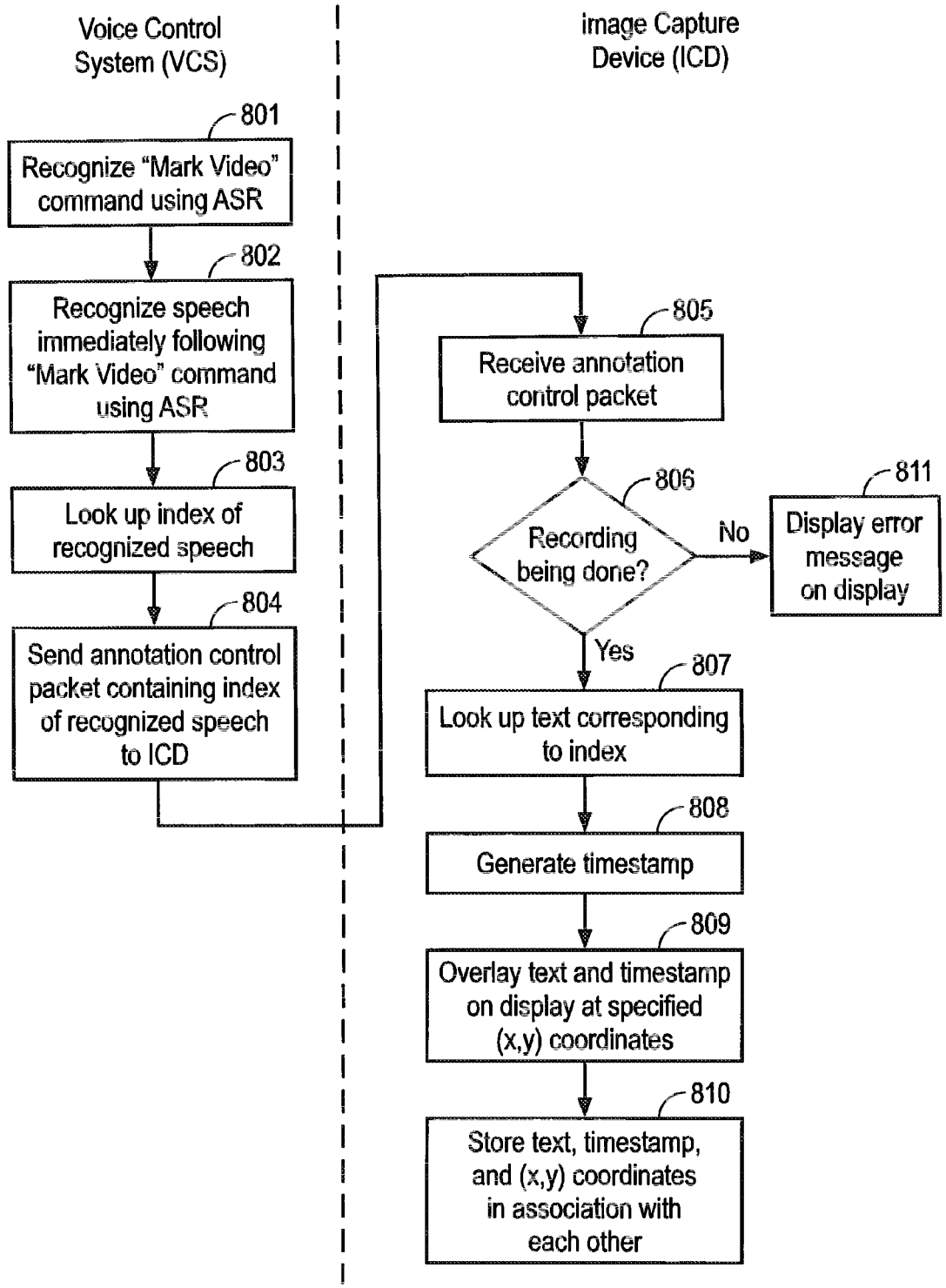
FIG. 8 is a flow diagram illustrating an example of a process of annotating video.

As will now be described, FIG. 8 shows an example of a process of annotating video according to certain embodiments of the invention. This process is normally performed on live video received from the camera 3. Nonetheless, previously recorded video can also be annotated in essentially the same manner. It is further assumed that multiple frames are always annotated (e.g., at least a predetermined minimum number of frames), since human sight or hearing would not likely perceive the annotation of just a single frame at normal speed.

Operations 801 through 804 are performed by the VCS 10, while operations 805 through 811 are performed by the ICD 15. Initially, at 801 the ASR engine 50 in the VCS 10 recognizes the predetermined annotation command spoken by the user, such as "Mark Video". The ASR engine 50 than recognizes the speech immediately following the command. The ASR engine 50 then looks up the index of that speech in annotation dictionary 64 at 803. At 804 the VCS 10 sends an annotation control packet (a control packet in which the indicated action is to annotate video) containing the index of the recognized speech the ICD 15.

At 805 the ICD 15 receives the annotation control packet from the VCS 10. If the received video is not currently being recorded (806), the ICD 15 causes an error message (e.g., "Not recording") to be displayed on the display device 9 at 811. If the video is being recorded, then at 807 the ICD 15 looks up the text corresponding to the index in the received control packet (i.e., the annotation's output value) in annotation dictionary 65. The ICD 15 then generates a timestamp at 808 and, at 809, overlays the text and the timestamp on the live video display at the (x,y) coordinates specified in the control packet (if any, otherwise at the default (x,y) coordinates). At 810, the ICD 15 stores the text of the indication, the timestamp, and the (x,y) coordinates in association with each other, using any of the association techniques described above. When the annotation is first overlaid on the live video display, the user may be provided with a brief timeout period during which he can confirm or cancel the annotation.

Non-text annotations, such as graphical objects, can also be associated with the video in a similar manner. In that case, it is desirable to have a set of predefined annotation objects from which the user can select, such as a pointer or a hollow shape to point to or outline a feature of interest. The selected annotation object can be associated with the video in a similar manner as described above. As noted above, the Action field 72 in a control packet sent from the VCS 10 to the ICD 15 indicates the type of annotation, i.e., text, object, audio, etc.

The annotation technique introduced herein also facilitates other advantageous techniques. For example, it is possible to generate an "album" display showing thumbnail versions of key video frames (i.e., frames that are annotated) from the recorded video. From the album display, a user can easily identify important frames, play back important segments of the video, and add, delete or edit the annotations associated with those frames.

Figure 9:
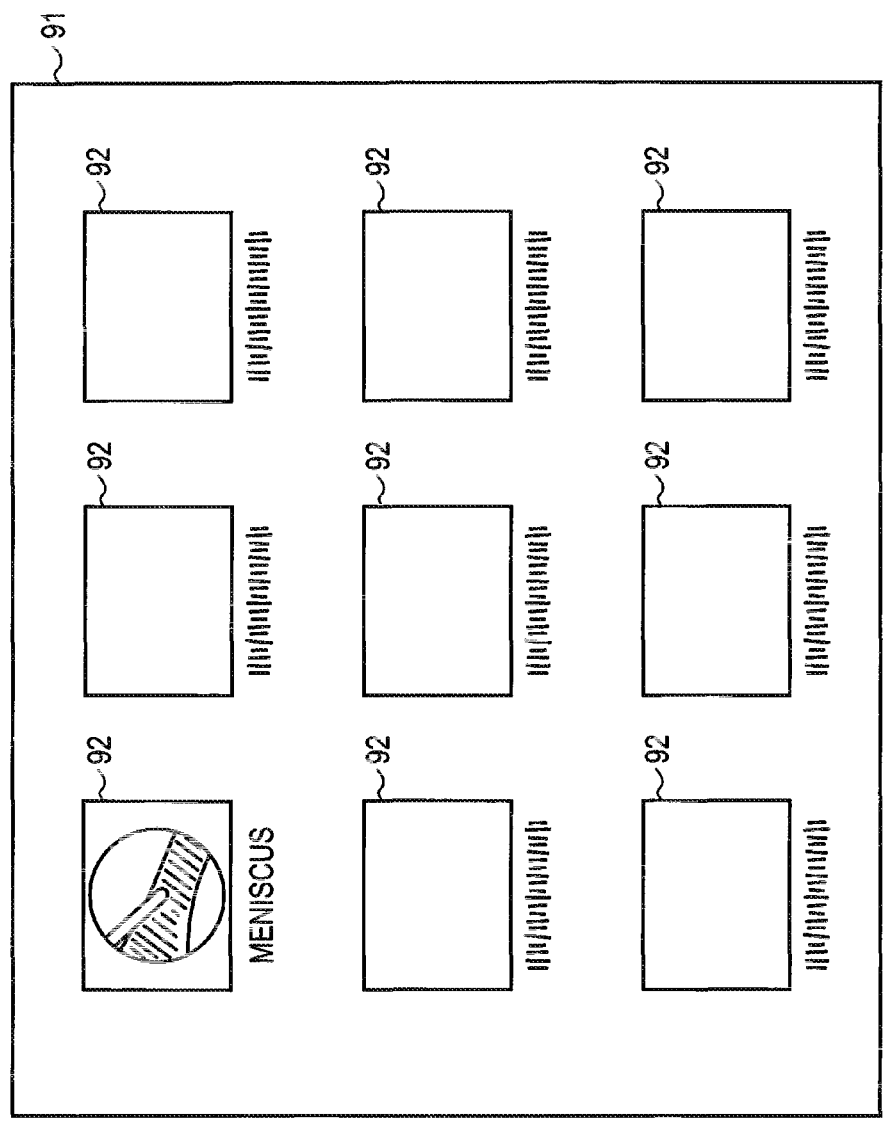
FIG. 9 shows an example of the album display.

FIG. 9 shows an example of the album display, which can be displayed on the external monitor 9, the display device of the ICD 15, or both. The album display 91 includes thumbnail images 92 of the frames that have been annotated, arranged in a matrix format. For frames annotated with text, the annotation associated with the frame is display directly below the thumbnail image 92 of the frame. In certain embodiments, the user can select a particular thumbnail image using the touchscreen of the ICD 15, a mouse, or any other available pointing device. This action may cause the full-sized version of that frame to be displayed or cause a segment of video associated with that frame to be played back (depending on user preference or preferred design and implementation). The user can also select the annotation under any particular thumbnail image and edit or delete that annotation using a keyboard or speech recognition. In a similar manner, non-text annotations can also be accessed, edited and/or deleted.

Figure 10:
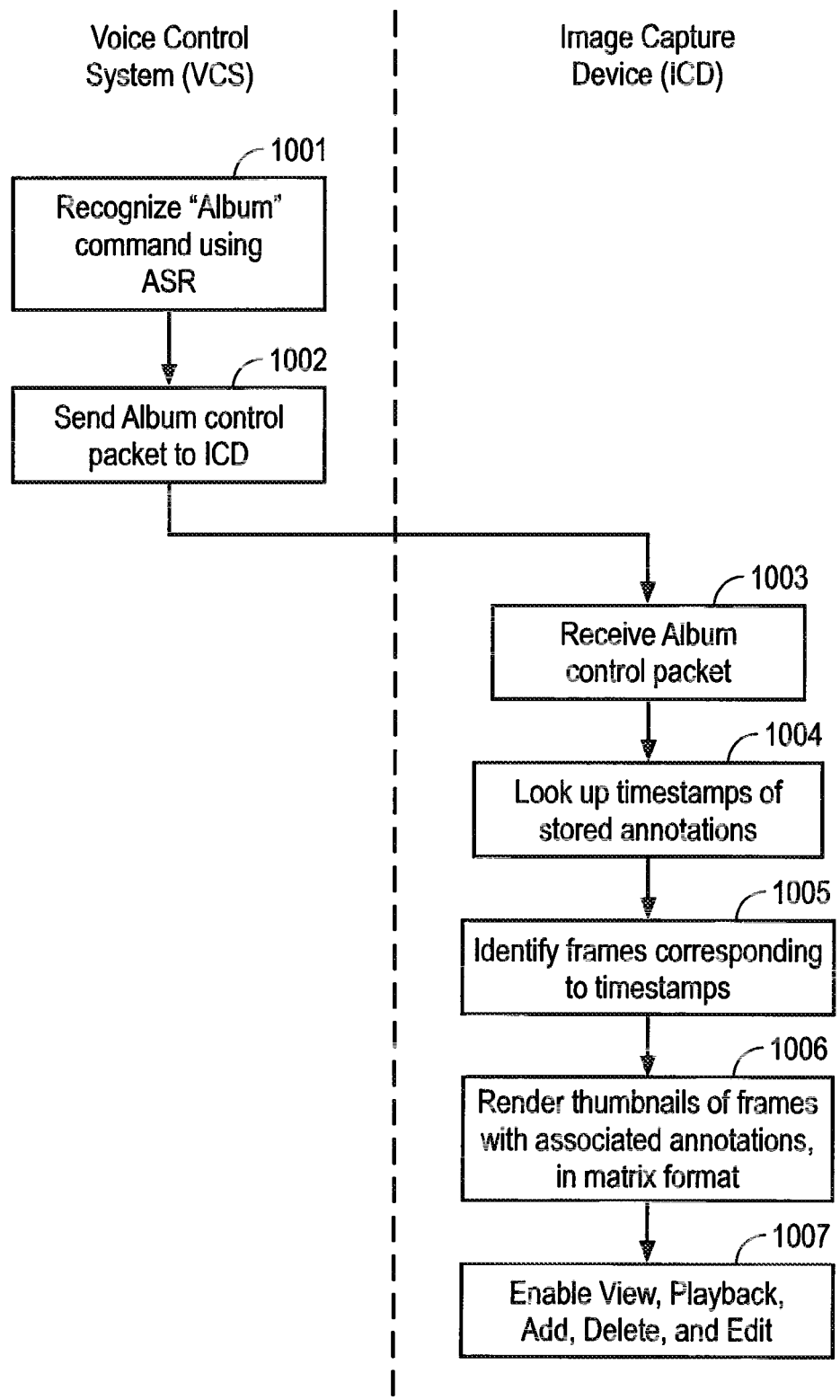
FIG. 10 is a flow diagram illustrating an example of a process of generating an album display from recorded annotated video.

FIG. 10 shows an example of a process of generating an album display from recorded, annotated video, according to certain embodiments of the invention. Operations 1001 and 1002 are performed by the VCS 10, while operations 1003 through 1007 are performed by the ICD 15. Initially, at 1001 the ASR engine 50 recognizes a predetermined command spoken by the user, such as "Album". In response, at 1002 the VCS 10 sends to the ICD 15 an album control packet, i.e., a control packet in which the Action field 72 indicates that the desired action is to generate an album display. At 1003 the ICD 15 receives the album control packet. The ICD 15 responds to the album control packet at 1004 by looking up the timestamps of all annotations that have been associated with the recorded video. At 1005 the ICD 15 identifies the frames which correspond to those timestamps. The ICD 15 then renders thumbnail images of the identified frames, i.e. the frames with associated annotations, in a matrix format such as shown in FIG. 9. The ICD 15 then enables the video viewing and playback modes for the displayed frames (thumbnails) and also enables adding, deleting, or editing of the annotations of the displayed frames. Of course, many variations and modifications of this process are possible.

The annotation technique introduced above also facilitates location of frames of particular interest in a recorded video without the need to review the entire recorded video. More specifically, the annotation technique allows quick and easy location and viewing of particular frames or video segments, by using a software based keyword search tool. For example, once the video has been annotated, a user can search the recorded annotated video stream for the annotation "gall bladder", with a software based keyword search tool, in order to locate frames that show the gall bladder. The search tool would parse the annotations at the end of the file for the video and do a simple lookup for the video frame/timecode within the video. It would then automatically take the video to the corresponding video frame.

Figure 11:
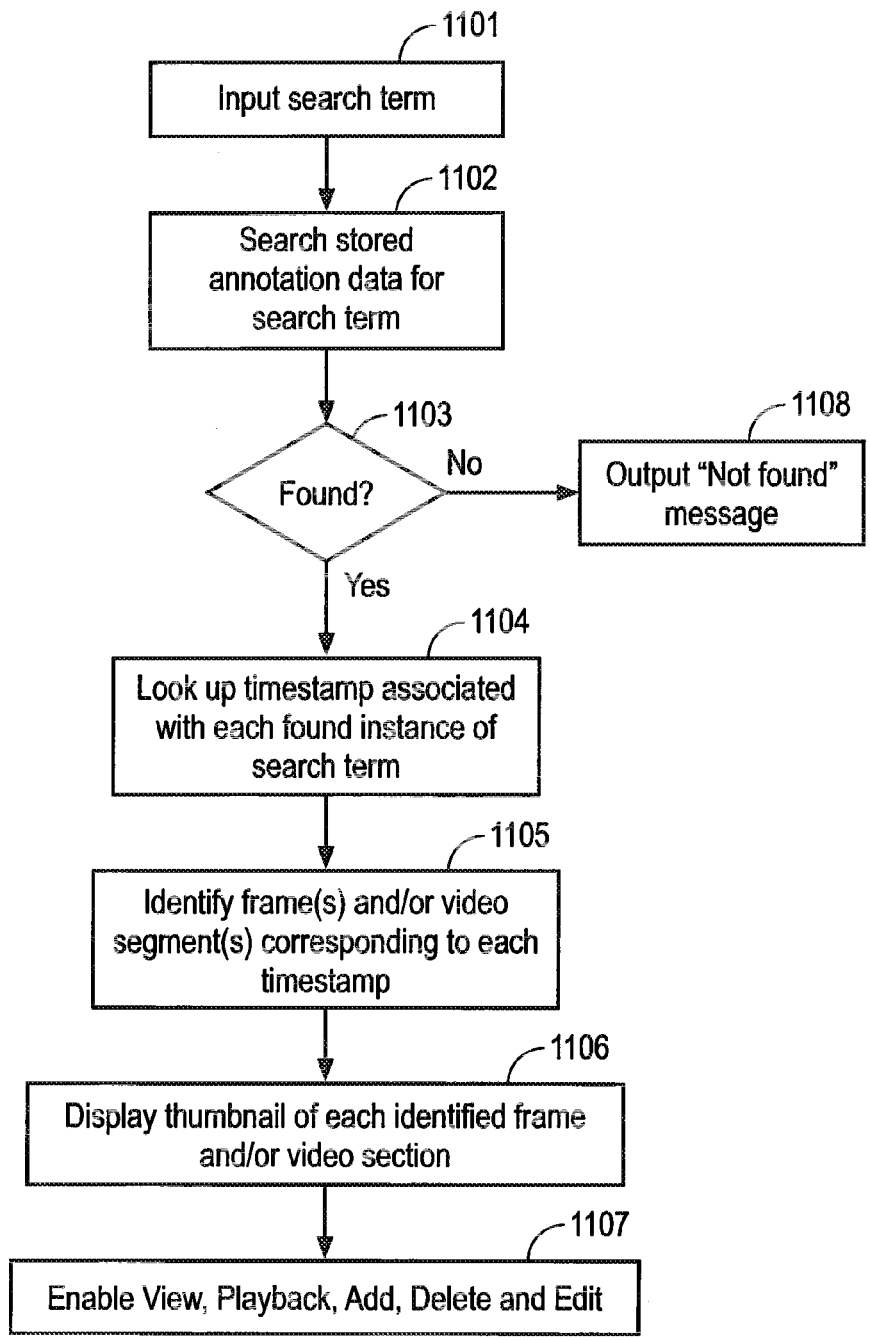
FIG. 11 is a flow diagram illustrating an example of a process of searching recorded annotated video for a particular term.

FIG. 11 shows an example of a process for searching annotated recorded video for a particular term, according to certain embodiments of the invention. This process can be performed by the ICD 15, for example, or by another processing device that has access to the annotated recorded video. At 1101, a search term is input from the user (for example, "gall bladder") through any suitable user interface. The annotation data associated with the recorded video (e.g., annotation storage 66 in FIG. 6) is then searched at 1102 for the input search term. If the search term is not found (1103) in the annotation data, then an appropriate error message, (e.g., "Not Found") is output to the user at 1108. If the search term is found in the annotation data, then at 1104 a lookup is done of the timestamp of each instance of the search term in the annotation data. At 1105 the frame(s) and/or video segment(s) corresponding to each timestamp are identified, and at 1106 a thumbnail image of each such frame and/or video section is displayed. The display may be the same or similar to that of FIG. 9, for example. At 1107, the video viewing and playback modes are enabled with respect to the displayed frames (thumbnails), and adding, deleting, or editing of the annotations of the displayed frames are also enabled.

Numerous variations and modifications of the above-described techniques are possible. For example, as described above, when the user wishes to annotate a frame of video, in certain embodiments the user speaks a known command, such as "Mark Video", to trigger the annotation function, and then immediately thereafter speaks the word or words that are the intended annotation, such as "gallbladder". In alternative embodiments, however, or as a user selectable option, the user could instead say a known command to cause a list of predefined annotations to be displayed on the monitor and then select one of the annotations from the list. In that case, the list of selectable annotations can be context sensitive, i.e., the particular annotations in the list are dependent upon the type of medical procedure currently being performed (information which can be input to the ICD before the start of the procedure). A different list of predefined annotations can be provided for any of multiple common procedures.

In yet another embodiment, or as another user selectable option, the user does not have to provide any command to annotate video. Instead, the system can be configured to automatically annotate the current frame or frames video upon recognizing certain keywords. For example, the system might be configured so that any time the term "ACL" is spoken by the user and recognized, the current frames are automatically annotated with that term.

Thus, a method and apparatus for to annotate video generated by an endoscopic camera in response to speech have been described. Although the present invention has been described with reference to specific exemplary embodiments, it will be recognized that the invention is not limited to the embodiments described, but can be practiced with modification and alteration within the spirit and scope of the appended claims. Accordingly, the specification and drawings are to be regarded in an illustrative sense rather than a restrictive sense.

What is claimed is:

1. A method comprising:
   receiving a video stream generated by an endoscopic video camera;
   receiving and automatically recognizing, by a voice-responsive control system, a spoken utterance of a user while the video stream is being received, wherein the spoken utterance includes a predefined command and additional speech, the voice-responsive control system looks up a non-text annotation corresponding to the additional speech and in response to recognizing the predefined command;
   sending, from the voice-responsive control system to an image capture device, a control packet including an indication that the annotation is a non-text visual object, an index of the annotation, and display coordinates for the annotation;
   providing, by the image capture device, the video stream and the annotation to a display device for display, such that the annotation is overlaid on a frame of the video stream displayed on the display device at the display coordinates specified by the control packet to point to or outline an anatomical feature; and
   associating, by the image capture device, the annotation with the video stream.

2. A method as recited in claim 1, further comprising recording the video stream, wherein associating the annotation with at least a portion of the video stream comprises associating the annotation with at least a portion of the recorded video stream.

3. A method as recited in claim 2, further comprising:
   in response to a predetermined input, identifying a set of one or more frames or sections of video in the recorded video stream, each of which has an annotation previously associated therewith; and
   generating an album display in which each frame in the set is displayed as a thumbnail image in proximity with the associated annotation.

4. A method as recited in claim 3, further comprising enabling a user to initiate playback of a segment of the recorded video stream from the album display by inputting a user input relating to a thumbnail image in the album display.

5. A method as recited in claim 3, further comprising enabling a user to edit one of the annotations from the album display.

6. A method as recited in claim 2, further comprising:
   inputting a search term specified by a user;
   searching a set of stored annotations associated with the recorded video stream for the search term; and
   if an annotation corresponding to the search term is found in the set of stored annotations, causing a visual representation of a segment of the recorded video stream associated with said annotation to be displayed to the user.

7. A method as recited in claim 1, further comprising:
   associating a second annotation that corresponds to a second spoken utterance with at least a second portion of the video stream, wherein the second annotation comprises a text object.

8. A method as recited in claim 1, wherein the non-text visual object is a pointer or hollow shape.

9. A method as recited in claim 1, further comprising:
   associating a second annotation that corresponds to a second spoken utterance with at least a second portion of the video stream, wherein the second annotation comprises an audio object.

10. A method as recited in claim 1, wherein the live video stream has no embedded audio, other than the annotation or other annotations similar to said annotation.

11. A method as recited in claim 1, wherein associating the annotation with the video stream comprises storing the annotation in a closed-caption portion of a frame of the video stream.

12. A method as recited in claim 1, wherein associating the annotation with the video stream comprises embedding the annotation in a video portion of a frame of the video stream.

13. A method as recited in claim 1, wherein associating the annotation with the video stream comprises appending the annotation to the end of the video stream.

14. A method as recited in claim 1, further comprising:
   outputting to an end user a context-sensitive list of user-selectable annotations usable for annotating the video, wherein said annotation is selected from the list by the user.

15. A method as recited in claim 14, wherein the context-sensitive list is configurable to include annotations specified by the end user.

16. A method as recited in claim 1, further comprising:
   storing a first dictionary containing an association of indexes and phonemes, wherein the index is identified from the first dictionary; and
   storing a second annotation dictionary containing an association of indexes and annotations, wherein the annotation is retrieved from the second dictionary based on the index.

17. A method as recited in claim 16, wherein at least one of the annotations is defined by an end user of the endoscopic system.

18. An apparatus comprising:
   a voice-responsive control system to
      receive a video stream generated by an endoscopic video camera;
      receive and automatically recognize a spoken utterance of a user while the video stream is being received, wherein the spoken utterance includes a predefined command and additional speech, the voice-responsive control system including an annotation dictionary to store a set of annotations,
      look up, in the annotation dictionary, a non-text annotation corresponding to the additional speech in response to recognizing the predefined command
      generate a control packet including an indication that the annotation is a non-text visual object, an index of the annotation, and display coordinates for the annotation; and
   an image capture device to
      receive the control packet and the video stream from the voice-responsive control system,
      provide the video stream and the annotation to a display device, such that the annotation is overlaid on a frame of the video stream displayed on the display device at the display coordinates specified by the control packet to point to or outline an anatomical feature, and associate the annotation with at least a portion of the video stream.

19. An apparatus as recited in claim 18, further comprising:
a video capture circuit to capture the video stream; and
a non-volatile mass storage device to store the captured video stream.

20. An apparatus as recited in claim 18, further comprising:
a network interface to enable the apparatus to transmit the video stream over a network;
a non-volatile mass storage device to store at least a portion of the video stream; and
a display device to display images from the video stream.

21. An apparatus as recited in claim 18, further comprising a video recording circuit to record the video stream, wherein the image capture device associates the annotation with the video stream by associating the annotation with the recorded video stream.

22. An apparatus as recited in claim 18, wherein the image capture device further associates a second annotation that corresponds to a second spoken utterance with at least a second portion of the video stream, wherein the second annotation comprises a text object.

23. An apparatus as recited in claim 18, wherein the non-text visual object is a pointer or hollow shape.

24. An apparatus as recited in claim 18, wherein the image capture device further associates a second annotation that corresponds to a second spoken utterance with at least a second portion of the video stream, wherein the second annotation comprises an audio object.

25. An apparatus as recited in claim 18, wherein at least one of the annotations is defined by an end user of the endoscopic system.

26. An apparatus as recited in claim 18, wherein the image capture device associates the annotation with the video stream by storing the annotation in a closed-caption portion of a frame.

27. An apparatus as recited in claim 18, wherein the image capture device associates the annotation with the video stream by embedding the annotation in a video portion of a frame.

28. An apparatus as recited in claim 18, wherein the image capture device associates the annotation with the video stream by appending the annotation to the end of the video stream.

* * * * *